(12) United States Patent
Yen et al.

(10) Patent No.: US 8,961,121 B2
(45) Date of Patent: Feb. 24, 2015

(54) CENTRIFUGAL FAN

(75) Inventors: Kevin Yen, Nagano (JP); Jiro Watanabe, Nagano (JP); Hiromitsu Kuribayashi, Nagano (JP); Shigekazu Mitomo, Nagano (JP)

(73) Assignee: Sanyo Denki Co., Ltd., Tokyo (JP)

( * ) Notice: Subject to any disclaimer, the term of this patent is extended or adjusted under 35 U.S.C. 154(b) by 791 days.

(21) Appl. No.: 13/166,148

(22) Filed: Jun. 22, 2011

(65) Prior Publication Data

US 2011/0318176 A1 Dec. 29, 2011

(30) Foreign Application Priority Data

Jun. 25, 2010 (JP) .................................. 2010-144863

(51) Int. Cl.
*F04D 29/44* (2006.01)
*F04D 25/06* (2006.01)
*F04D 29/42* (2006.01)
*F04D 29/66* (2006.01)

(52) U.S. Cl.
CPC .......... *F04D 25/0613* (2013.01); *F04D 29/422* (2013.01); *F04D 29/667* (2013.01)
USPC .......... 415/204; 415/206; 415/207; 415/212.1

(58) Field of Classification Search
CPC ......... F04D 5/007; F04D 5/008; F04D 17/04; F04D 29/422; F04D 29/428; F04D 29/4293; F04D 29/545; F04D 29/547
USPC ........... 415/204, 182.1, 203, 206, 207, 208.1, 415/212.1
See application file for complete search history.

(56) References Cited

U.S. PATENT DOCUMENTS

| 6,254,336 B1 | 7/2001 | Ahn |
| 2003/0049122 A1 | 3/2003 | Kim et al. |
| 2004/0165984 A1 | 8/2004 | Ochiai et al. |
| 2004/0253092 A1 | 12/2004 | Hancock |

(Continued)

FOREIGN PATENT DOCUMENTS

| CN | 1348065 | 5/2002 | |
| EP | 1375925 A2 * | 1/2004 | .............. F04D 29/58 |

(Continued)

OTHER PUBLICATIONS

Japanese Office Action with English translation dated Mar. 18, 2014, 5 pages.

(Continued)

*Primary Examiner* — Edward Look
*Assistant Examiner* — Maxime Adjagbe
(74) *Attorney, Agent, or Firm* — Rankin, Hill & Clark LLP

(57) ABSTRACT

A casing of a centrifugal fan includes a suction port forming wall portion, an opposed wall portion opposed to the suction port forming wall portion, and a sidewall portion connecting the suction port forming wall portion and the opposed wall portion. A tongue portion is provided at the sidewall portion. The tongue portion projects into an air passage in the vicinity of a discharge port to form a narrowed air passage portion within the air passage. A leading end surface of the tongue portion is shaped such that the width of the leading end surface increases from the suction port forming wall portion, where the suction port is formed, to the opposed wall portion. The tongue portion is shaped such that the projecting length of the tongue portion into the air passage continuously decreases from the suction port forming wall portion to the opposed wall portion.

1 Claim, 4 Drawing Sheets

(56) References Cited

U.S. PATENT DOCUMENTS

| | | | |
|---|---|---|---|
| 2005/0214114 A1* | 9/2005 | Huang et al. | ................. 415/206 |
| 2009/0169373 A1 | 7/2009 | Hwang et al. | |
| 2010/0040456 A1 | 2/2010 | Hwang et al. | |
| 2010/0104421 A1 | 4/2010 | Hwang et al. | |

FOREIGN PATENT DOCUMENTS

| | | |
|---|---|---|
| JP | 07-14192 U | 3/1995 |
| JP | 2003-074497 | 3/2003 |
| JP | 2004-218446 | 8/2004 |
| JP | 2009-287427 | 12/2009 |
| TW | 200532424 | 10/2005 |

OTHER PUBLICATIONS

Chinese Office Action with English Translation dated Nov. 3, 2014, 13 pages.

* cited by examiner

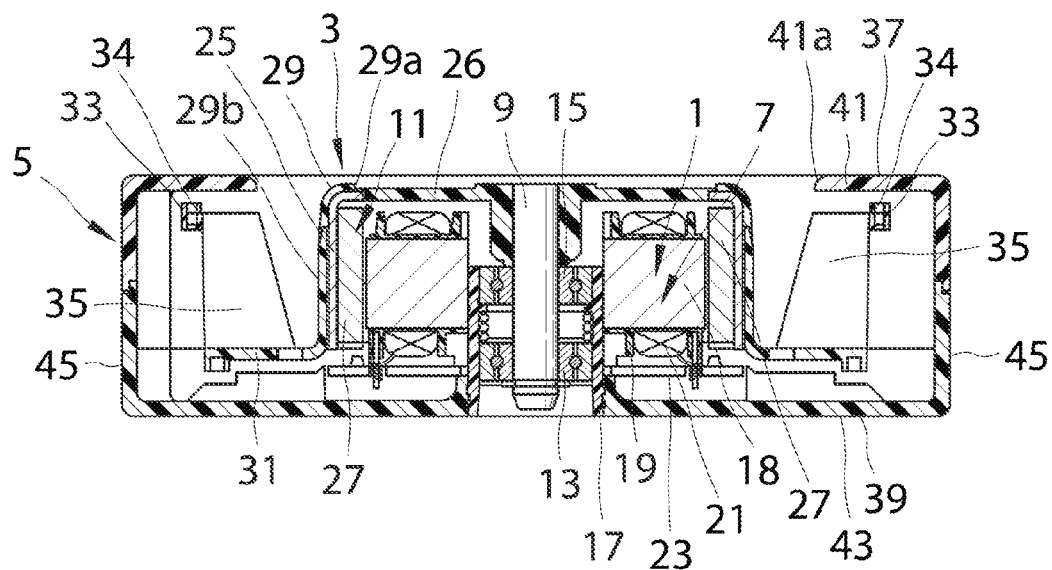
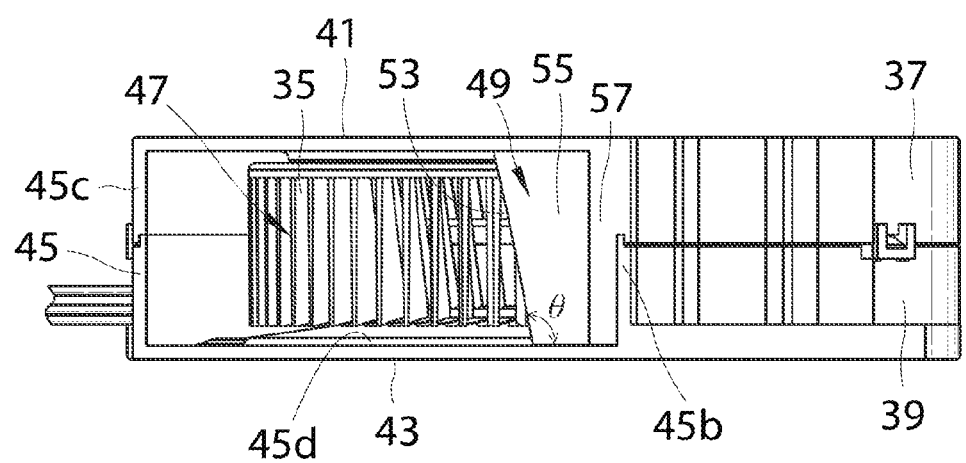

CENTRIFUGAL FAN

BACKGROUND OF THE INVENTION

The present invention relates to a centrifugal fan.

A centrifugal fan disclosed in Japanese Utility Model Application Publication No. 7-14192 (JPU7-14192A) comprises an electric motor, an impeller and a volute casing. The impeller includes a plurality of blades and is fixed to a rotary shaft of the electric motor to rotate therewith. The casing includes therein a scroll air passage extending from a suction port to a discharge port, and is configured to receive the impeller in the air passage. The scroll air passage is formed such that the sectional area of the scroll air passage gradually increases toward the discharge port in the vicinity of the discharge port. A tongue portion is provided at the casing. The tongue portion projects into the air passage in the vicinity of the discharge port to form a narrowed air passage portion within the air passage. The projecting length of the tongue portion into the air passage changes stepwise along an axial direction of the rotary shaft.

SUMMARY OF THE INVENTION

In conventional centrifugal fans, attempts have been made to reduce noise by modifying the shape of the tongue portion provided in each fan. However, it is still demanded that noise be further reduced without degrading an airflow—static pressure characteristic.

An object of the present invention is to provide a centrifugal fan in which noise may be reduced, without degrading an airflow—static pressure characteristic.

A centrifugal fan, improvement of which is aimed at by the present invention, comprises an electric motor including a rotary shaft, an impeller, and a casing. The impeller includes a plurality of blades and is directly or indirectly fixed to the rotary shaft of the electric motor to rotate therewith. The casing has a suction port, a discharge port, and a scroll air passage communicating with the suction port, and is configured to receive the impeller in the air passage. Then, the casing includes: a suction port forming wall portion where the suction port is formed to open in an axial direction of the rotary shaft; an opposed wall portion opposed to the suction port forming wall portion; a sidewall portion connecting the suction port forming wall portion and the opposed wall portion to define the scroll air passage; and a tongue portion provided at the sidewall portion. The tongue portion projects into the air passage in the vicinity of the discharge port to form a narrowed air passage portion within the air passage. In the present invention, the tongue portion is shaped such that the projecting length of the tongue portion into the air passage continuously decreases from the suction port forming wall portion to the opposed wall portion.

The inventors of the present invention have found that, when the tongue portion includes steps as in conventional centrifugal fans, noise cannot be reduced unless the size of each step is appropriately determined. Otherwise, noise may increase. The inventors have then found that noise may be reliably reduced when the projection length of the tongue portion continuously decreases as in the present invention. Accordingly, by shaping the tongue portion as in the present invention, noise may be reduced without degrading an airflow—static pressure characteristic. The reason for reduced noise is considered to be that when the rotating impeller passes by the vicinity of the tongue portion, a pressure variation may be reliably reduced due to the continuous decrease in projection length of the tongue portion into the air passage from the suction port forming wall portion to the opposed wall portion.

Preferably, the projecting length of the tongue portion may decrease at a constant rate. With this arrangement, designing the tongue portion is facilitated.

Preferably, the tongue portion may include a leading end surface which is shaped such that the width of the leading end surface increases from the suction port forming wall portion to the opposed wall portion. With this arrangement, when the rotating impeller passes by the vicinity of the tongue portion, pressure variation may be reduced more reliably than when the width is set to be constant.

Preferably, the tongue portion may include a leading end surface which is shaped to have an arc section, as cut in a direction orthogonal to the axial direction of the rotary shaft, or as cut along a virtual plane perpendicular to an axial line of the rotary shaft. Further, the arc section of the leading end surface has a radius which gradually increases from the suction port forming wall portion to the opposed wall portion. With this arrangement, the width of the leading end surface smoothly increases from the suction port forming wall portion to the opposed wall portion.

Preferably, the tongue portion may include an inclined surface continuous with the leading end surface and inclined to make the air passage wider toward the discharge port. If such an inclined surface is provided, air, which has flown through the narrowed air passage portion, may flows along the inclined surface. The air may be then smoothly flown to the discharge port. Noise may thereby be further reduced.

Preferably, the inclined surface may include a first inclined surface portion continuous with the leading end surface and inclined at a given inclination angle and a second inclined surface portion continuous with the first inclined surface portion and curved to be convex toward the air passage. With this arrangement, air flowing to the discharge port along the inclined surface may be more smoothly flown.

Preferably, the tongue portion may further include a flat surface continuous with the second inclined surface portion and extending along the discharge port. With this arrangement, a part of air, which has passed over the inclined surface, flows over the flat surface and is then smoothly discharged from the discharge port.

BRIEF DESCRIPTION OF THE DRAWINGS

These and other objects and many of the attendant advantages of the present invention will be readily appreciated as the same becomes better understood by reference to the following detailed description when considered in connection with the accompanying drawings.

FIG. 2 is a sectional view as taken along line II-II in FIG. 1.

FIG. 3 is a side view of a casing of the centrifugal fan shown in FIG. 1.

DETAILED DESCRIPTION OF PREFERRED EMBODIMENT

Figure 1:
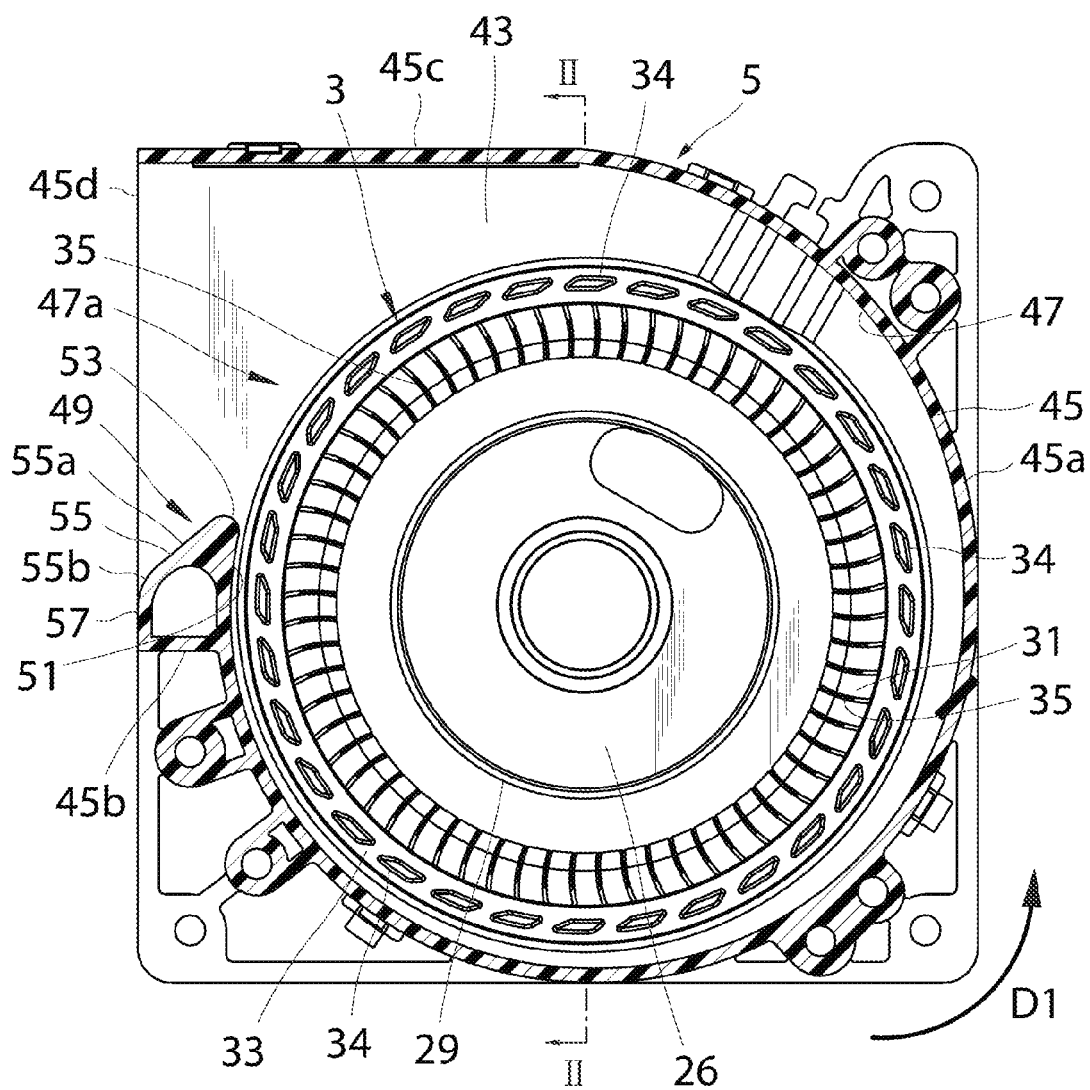
FIG. 1 illustrates a centrifugal fan according to an embodiment of the present invention, wherein a suction port forming wall portion is omitted from the illustration.

An example of an embodiment of the present invention will be described below in detail with reference to the drawings. FIG. 1 illustrates a centrifugal fan according to an embodiment of the present invention wherein a suction port forming wall portion, which will be described later, is omitted from the illustration. FIG. 2 is a sectional view of the centrifugal fan as taken along line II-II in FIG. 1, with the suction port forming wall portion shown in the view. As shown in both of FIGS. 1 and 2, the centrifugal fan (sirocco fan) of this embodiment comprises an electric motor 1, an impeller 3 configured to be rotated by the electric motor 1, and a casing 5 configured to receive the impeller 3.

As shown in FIG. 2, the electric motor 1 includes a stator 7, a rotary shaft 9, and a rotor 11. The stator 7 is fitted on a bearing holder 17. Two ball bearings 13 and 15 for rotatably supporting the rotary shaft 9 are fittedly held in the bearing holder 17. The stator 7 includes a stator core 18, an insulator 19 made of an insulating resin, and a plurality of stator windings 21. The stator core 18 is disposed outward of the bearing holder 17 in a radial direction of the rotary shaft. The insulator 19 is fitted with the stator core 18. The stator windings 21 are wound on a plurality of magnetic pole portions of the stator core 18 via the insulator 19. The stator windings 21 are each electrically connected to a circuit pattern, not shown, on a circuit board 23 through a connecting conductor. A drive circuit is mounted on the circuit board 23 for supplying an exciting current to the stator windings 21. The rotor 11 includes an annular permanent magnet support member 25 made of a magnetic material such as iron, a metal hub 26 fixed to one end of the rotary shaft 9, and a plurality of permanent magnets 27 fixed to an inner peripheral portion of the permanent magnetic support member 25 and opposed to the stator core 18. In this embodiment, the permanent magnet support member 25 and the hub 26, which have been formed individually, are combined to form a cup-like member. Of course, the cup-like member may unitarily be formed.

The impeller 3 which is rotated by the electric motor 1 is unitarily formed of a synthetic resin, including an impeller body 29, a blade support portion 31, a blade mounting portion (shroud) 33, and a plurality of blades 35. In this embodiment, the impeller 3 rotates in an anticlockwise direction (indicated by arrow D1) on the page of FIG. 1 as a direction of normal rotation.

The impeller body 29 has an opening portion 29a formed therein to expose a part of the metal hub 26 and includes a cylindrical peripheral wall portion 29b fitted on the permanent magnet support member 25. Of course, the impeller body 29 may be formed in a bottomed cylindrical shape without the opening portion 29a, entirely covering the hub 26.

The blade support portion 31 has an annular shape, and extends from an end portion of the peripheral wall portion 29b of the impeller body 29 in a radially outward direction of the rotary shaft 9. The blades 35 projecting toward the suction port forming wall portion 41 are provided at the blade support portion 31. The blades 35 are shaped such that air sucked from a suction port 41a, which will be described later, is discharged in a radial direction of the rotary shaft 9 when the impeller 3 rotates in the direction of normal rotation. The blade mounting portion 33 has an annular shape, and connects end portions of the blades 35 located on the side of the suction port forming wall portion 41. In this embodiment, the blade mounting portion 33 is located radially outward of the end portions of the blades 35. Further, the blade mounting portion 33 is located radially outward of the suction port 41a. Accordingly, the blade mounting portion 33 cannot be seen through the suction port 41a. As shown in FIG. 1, a plurality of balance weight fitting holes 34 are formed in an end surface portion of the blade mounting portion 33 on the side of the suction port forming wall portion 41 at equidistant intervals in a peripheral direction of the shroud 33. In this embodiment, both ends of the elongated balance weight fitting holes 34 in the circumferential direction are inclined in a direction opposite to the rotation direction of the impeller 3. If both ends of the elongated balance weight fitting holes 34 are inclined in this manner, air resistance of the balance weight fitting holes 34 decreases when the impeller 3 rotates.

The casing 5 for receiving the impeller 3 is formed by combining a first casing half portion 37 and a second casing half portion 39 each formed of a synthetic resin, as shown in FIG. 2 and FIG. 3 which is a side view of the casing 5. With the first casing half portion 37 and the second casing half portion 39 combined, the casing 5 includes the suction port forming wall portion 41, an opposed wall portion 43 opposed to the suction port forming wall portion 41, and a sidewall portion 45 connecting the suction port forming wall portion 41 and the opposed wall portion 43. The suction port 41a, which is circular in shape, is formed at the center of the suction port forming wall portion 41. The suction port 41a opens toward one end of the axial direction of the rotary shaft 9 to suck air from an outside. Further, as shown in FIG. 1, the sidewall portion 45 includes a first sidewall portion 45a extending in an arc, a second sidewall portion 45b extending flatly from an end portion of the first sidewall portion 45a, which is located forward in the rotation direction of the impeller 3, and a third sidewall portion 45c extending flatly from an end portion of the first sidewall portion 45a, which is located rearward in the rotation direction of the impeller 3. Then, a discharge port 45d is formed to open in a direction orthogonal to the axial direction of the rotary shaft or a tangent direction of the impeller 3 between an end portion of the second sidewall portion 45b and an end portion of the third sidewall portion 45c. With such a configuration, a scroll air passage 47 communicating with the discharge port 45d and the suction port 41a is defined inside the casing 5.

Then, as shown in FIGS. 1 and 3, a tongue portion 49 projecting toward the third sidewall portion 45c is formed at the second sidewall portion 45b and the tongue portion 49 is continuous with the first sidewall portion 45a. In other words, the tongue portion 49 is provided at the sidewall portion 45, projecting into the air passage 47 in the vicinity of the discharge port 45d to form a narrowed air passage portion 47a within the air passage 47. The narrowed air passage portion 47a within the air passage 47 is a portion which is defined between a leading end surface 53 of the tongue portion 49 and the third sidewall portion 45c and in which the width of the air passage is narrowed.

The tongue portion 49 extends between the suction port forming wall portion 41 and the opposed wall portion 43. In this embodiment, the tongue portion 49 is unitarily formed with the first casing half portion 37. Alternatively, the tongue portion 49 may be halved, and halved tongue portions thus obtained may be unitarily formed with the first casing half portion 37 and the second casing half portion 39, respectively. Then, the tongue portion 49 may be formed by combining the first casing half portion 37 and the second casing half portion 39.

Figure 4:
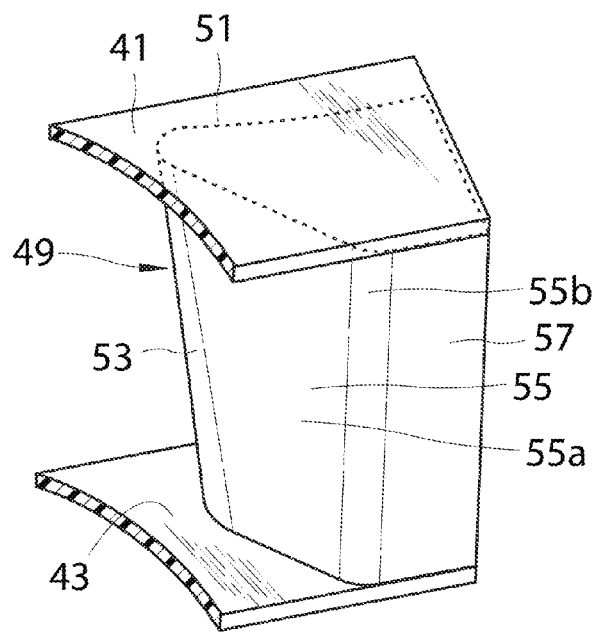
FIG. 4 is a perspective view of a tongue portion as seen from the suction port forming wall portion of the centrifugal fan shown in FIG. 1.
Figure 5:
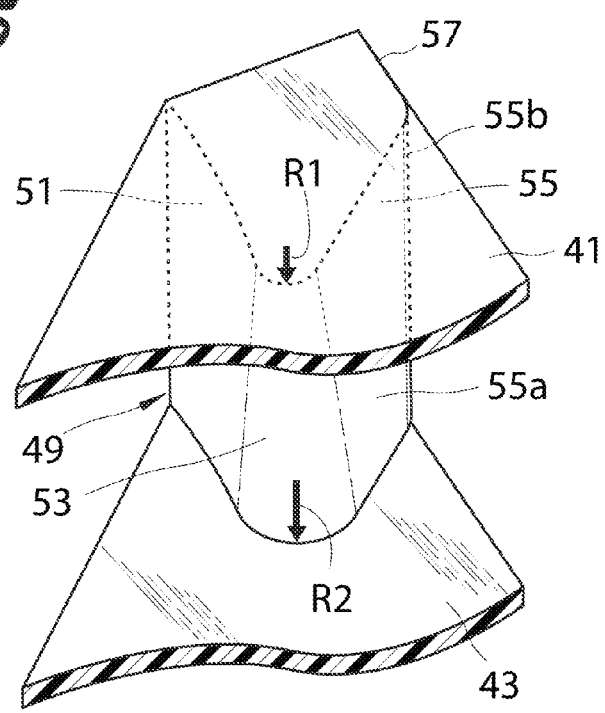
FIG. 5 is a perspective view of the tongue portion as seen at an angle different from that in FIG. 4.

The tongue portion 49 has substantially a trapezoidal section as cut in a direction orthogonal to the axial direction of the rotary shaft 9 or as cut along a virtual plane perpendicular to an axial line of the rotary shaft, as shown in FIGS. 4 and 5. The tongue portion 49 includes four continuous surfaces each exposed in the air passage 47, namely, an impeller opposed surface 51, the leading end surface 53, an inclined surface 55, and a flat surface 57. FIGS. 4 and 5 are perspective views each showing the tongue portion 49 as seen from the suction port forming wall portion 41. In the figures, a part of the suction port forming wall portion 41 and a part of the opposed wall portion 43 are also shown. As shown in FIG. 1, the impeller opposed surface 51 extends continuous with an inner surface of the first sidewall portion 45a extending in an arc, and is opposed to the impeller 3. The inclined surface 55 is continuous with the leading end surface 53 and is inclined to make the air passage 47 wider toward the discharge port 45d. The inclined surface 55 includes a first inclined surface portion 55a continuous with the leading end surface 53 and inclined at a given inclination angle, and a second inclined surface portion 55b continuous with the first inclined surface portion 55a and curved to be convex toward the air passage 47. The flat surface 57 is continuous with the second inclined surface portion 55b and extends along the discharge port 45d.

The leading end surface 53 located between the impeller opposed surface 51 and the inclined surface 55 has an arc section as cut along the direction orthogonal to the axial direction of the rotary shaft 9 or as cut along the virtual plane perpendicular to the axial line of the rotary shaft. As shown in FIG. 5, the arc section of the leading end surface 53 has a radius which gradually increases from the suction port forming wall portion 41 to the opposed wall portion 43. In this embodiment, a radius R1 of the arc section on the side of the suction port forming wall portion 41 is 2 mm, while a radius R2 of the arc section on the side of the opposed wall portion 43 is 4 mm. For this reason, the leading end surface 53 is shaped such that the width of the leading end surface 53 increases from the suction port forming wall portion 41 to the opposed wall portion 43. As shown in FIGS. 3 and 4, the leading end surface 53 is inclined to gradually get away from the third sidewall portion 45c in a direction from the suction port forming wall portion 41 to the opposed wall portion 43. In other words, the tongue portion 49 is shaped such that the projecting length of the tongue portion 49 into the air passage 47 continuously decreases at a constant rate from the suction port forming wall portion 41 to the opposed wall portion 43. In this embodiment, an angle θ formed between the leading end surface 53 and the opposed wall portion 43, shown in FIG. 3, is set to 100°.

Figure 6:
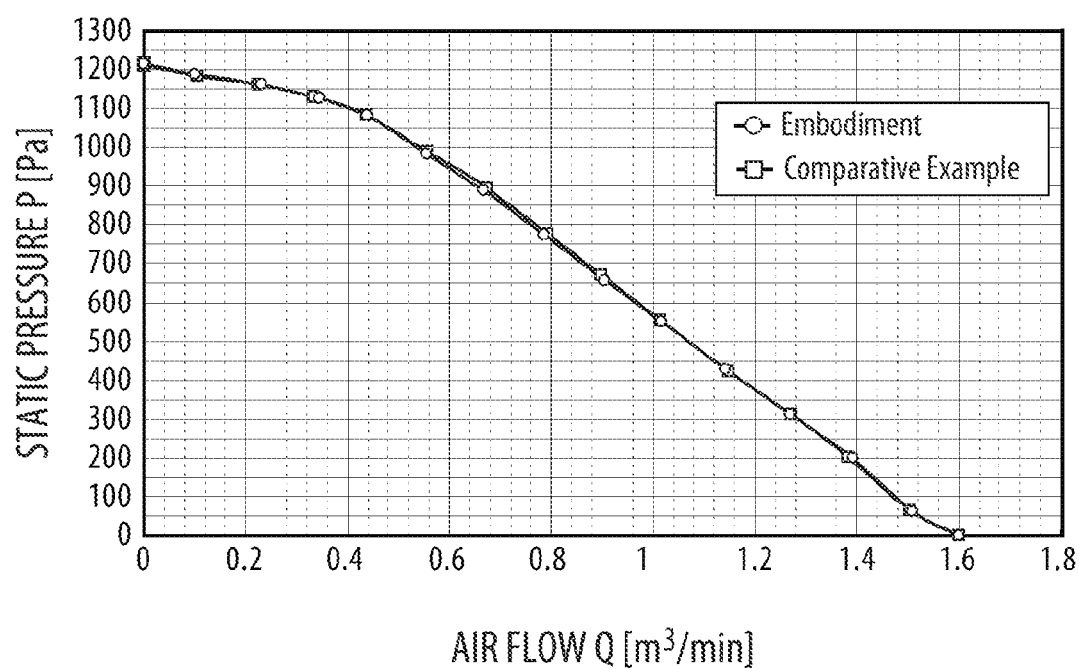
FIG. 6 is a graph showing relationships between airflow rates and static pressures in the centrifugal fan of the present invention and a centrifugal fan of a comparative example for testing.

Next, the centrifugal fan of the embodiment and a centrifugal fan of a comparative example were prepared, and a relationship between an airflow rate and a static pressure of each centrifugal fan and noise produced by each fan were then examined. The centrifugal fan of the embodiment is the one shown in FIGS. 1 to 5. The centrifugal fan of the comparative example is provided with a tongue portion including a leading end surface having an arc section. In the centrifugal fan of the comparative example, the radius of the arc section is constant from a suction port forming wall portion to an opposed wall portion, and the leading end surface is not inclined. The angle formed between the leading end surface and the opposed wall portion, corresponding to the angle θ in FIG. 3, is set to 90°. In the centrifugal fan of the comparative example, the radius of the leading end surface of the tongue portion is the same as the radius R1 (2 mm) on the side of the suction port forming wall portion 41 of the centrifugal fan of the embodiment. A joint position between a top of the leading end surface of the tongue portion and the suction port forming wall portion in the centrifugal fan of the comparative example and a joint position between a top of the leading end surface 53 of the tongue portion and the suction port forming wall portion 41 in the centrifugal fan of the embodiment are the same. The other components of the centrifugal fan of the comparative example have the same structures as those of the centrifugal fan of the embodiment. Next, the impeller of the centrifugal fan of the embodiment was rotated approximately at a rate of 5000 rpm. Also, the impeller of the centrifugal fan of the comparative example was rotated approximately at a rate of 5000 rpm. Then, the relationship between the airflow rate and the static pressure of each centrifugal fan was examined. FIG. 6 is a graph showing measurement results. It can be known from FIG. 6 that in both centrifugal fans of the embodiment and the comparative example, the static pressure values with respect to the airflow rates are substantially equal (airflow—static pressure characteristics are substantially the same).

In a free-air condition with a maximum airflow rate, the centrifugal fan of the embodiment produced a noise of 69.7 dB, and the centrifugal fan of the comparative example produced a noise of 70.2 dB. It was confirmed that the noise produced by the centrifugal fan of the embodiment was reduced from the noise produced by the centrifugal fan of the comparative example by 0.5 dB.

It follows from the foregoing that the centrifugal fan of the embodiment may produce less noise without reducing the static pressure value with respect to the airflow rate, compared with the centrifugal fan of the comparative example.

It has been confirmed by simulation that noise produced by the centrifugal fan, which employs a tongue portion having steps formed therein as disclosed in Japanese Utility Model Application Publication No. 7-14192, in a free-air condition is between the noise produced by the centrifugal fan of the embodiment and the noise produced by the centrifugal fan of the comparative example.

While the preferred embodiments of the invention have been described with a certain degree of particularity with reference to the drawings, obvious modifications and variations are possible in light of the above teachings. It is therefore to be understood that within the scope of the appended claims, the invention may be practiced otherwise than as specifically described.

What is claimed is:

1. A centrifugal fan comprising:
   an electric motor including a rotary shaft:
   an impeller including a plurality of blades and directly or indirectly fixed to the rotary shaft of the electric motor to rotate therewith; and
   a casing having a suction port, a discharge port, and a scroll air passage communicating with the suction port, and configured to receive the impeller in the air passage, the casing including:
      a suction port forming wall portion where the suction port is formed to open in an axial direction of the rotary shaft;
      an opposed wall portion opposed to the suction port forming wall portion;
      a sidewall portion connecting the suction port forming wall portion and the opposed wall portion to define the scroll air passage; and
      a tongue portion provided at the sidewall portion, projecting into the air passage in the vicinity of the discharge port to form a narrowed air passage portion within the air passage, and shaped such that the projecting length of the tongue portion into the air passage continuously decreases from the suction port forming wall portion to the opposed wall portion;
   the projecting length of the tongue portion decreases at a constant rate;

the tongue portion includes a leading end surface shaped such that the width of the leading end surface increases from the suction port forming wall portion to the opposed wall portion;

the tongue portion includes the leading end surface shaped to have an arc section, as cut in a direction orthogonal to the axial direction of the rotary shaft;

the arc section of the leading end surface has a radius which gradually increases from the suction port forming wall portion to the opposed wall portion;

the tongue portion includes an inclined surface continuous with the leading end surface and inclined to make the air passage wider toward the discharge port;

the inclined surface includes a first inclined surface portion continuous with the leading end surface and inclined at a given inclination angle and a second inclined surface portion continuous with the first inclined surface portion and curved to be convex toward the air passage; and the tongue portion further includes a flat surface continuous with the second inclined surface portion and extending along the discharge port.

\* \* \* \* \*